United States Patent
Lee et al.

(10) Patent No.: US 9,339,375 B2
(45) Date of Patent: May 17, 2016

(54) CAPSULE EXPANDER DEVICES, SYSTEMS, AND METHODS FOR INHIBITING CAPSULAR OPACIFICATION AND STABILIZING THE CAPSULE

(71) Applicant: Novartis AG, Basel (CH)

(72) Inventors: Sung Kyu Lee, Euless, TX (US); Son Trung Tran, Arlington, TX (US); Kevin Mark Lewellen, Arlington, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/102,563

(22) Filed: Dec. 11, 2013

(65) Prior Publication Data

US 2014/0172089 A1    Jun. 19, 2014

Related U.S. Application Data

(60) Provisional application No. 61/738,165, filed on Dec. 17, 2012.

(51) Int. Cl.
*A61F 2/16*    (2006.01)

(52) U.S. Cl.
CPC .................... *A61F 2/1694* (2013.01)

(58) Field of Classification Search
USPC ........................ 623/4.1, 6.38–6.41
See application file for complete search history.

(56) References Cited

U.S. PATENT DOCUMENTS

| | | | |
|---|---|---|---|
| 4,710,194 A | 12/1987 | Kelman | |
| 2005/0085907 A1* | 4/2005 | Hanna | 623/6.37 |
| 2005/0209692 A1* | 9/2005 | Zhang | 623/6.34 |
| 2010/0204790 A1 | 8/2010 | Whitsett | |
| 2010/0228344 A1* | 9/2010 | Shadduck | 623/6.18 |
| 2011/0082543 A1 | 4/2011 | Soll et al. | |

FOREIGN PATENT DOCUMENTS

EP    0337390    * 10/1986    ................ A61F 2/16

OTHER PUBLICATIONS

Tsutomu Hara et al., "Preventing Posterior Capsular Opacification with an Endocapsular Equator Ring in a Young Human Eye" Arch Opthalmol, vol. 125, Apr. 2007, pp. 483-486.
Toshiyuki Nagamoto et al., "Inhibition of Posterior Capsule Opacification by a Capsular Adhesion-Preventing Ring" Arch Opthalmol, vol. 127, Apr. 2009, pp. 471-474.
H. Burkhard Dick M.D., "Closed Foldable Capsular Rings" J. Cataract Refract Surg., vol. 31, Mar. 2005, pp. 467-471.
International Search Report and Written Opinion issued for PCT/US2013/074647 dated Mar. 5, 2014, 8 pgs.

* cited by examiner

*Primary Examiner* — David H Willse
*Assistant Examiner* — Tiffany Shipmon
(74) *Attorney, Agent, or Firm* — Haynes and Boone, LLP (57) ABSTRACT

Disclosed herein is an implantable capsule expander device for insertion within a lens capsule of an eye of a patient. The device comprises an arcuate center portion including first and second rims and having a first height, an outermost peripheral portion including a second height that is less than the first height, and a receiving portion formed between the first and second rims. The center portion and the outermost peripheral portion are configured to stabilize the capsule expander device within the lens capsule and to expand the lens capsule. The receiving portion is sized to receive an artificial intraocular lens.

19 Claims, 9 Drawing Sheets

CAPSULE EXPANDER DEVICES, SYSTEMS, AND METHODS FOR INHIBITING CAPSULAR OPACIFICATION AND STABILIZING THE CAPSULE

PRIORITY CLAIM

This application claims the benefit of priority of U.S. Provisional Patent Application Ser. No. 61/738,165 titled "CAPSULE EXPANDER DEVICES, SYSTEMS, AND METHODS FOR INHIBITING CAPSULAR OPACIFICATION AND STABILIZING THE CAPSULE," filed on Dec. 17, 2012, whose inventors are Sung Kyu Lee, Kevin Mark Lewellen and Son Trung Tran, which is hereby incorporated by reference in its entirety as though fully and completely set forth herein.

BACKGROUND

Visually impairing cataract, or clouding of the lens, is the leading cause of preventable blindness in the world. Presently, cataracts are treated by surgical removal of the affected lens and replacement with an artificial intraocular lens ("IOL"). Cataract extractions are among the most commonly performed operations in the world.

Figure 1:
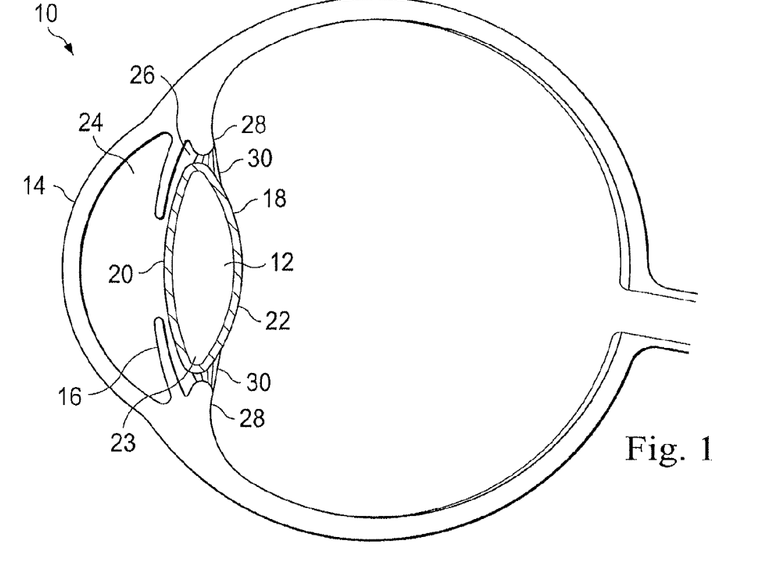
FIG. 1 is a diagram of a cross-sectional side view of an eye.

FIG. 1 is a diagram of an eye 10 showing some of the anatomical structures related to the surgical removal of cataracts and the implantation of IOLs. The eye 10 comprises an opacified lens 12, an optically clear cornea 14, and an iris 16. A lens capsule or capsular bag 18, located behind the iris 16 of the eye 10, contains the opacified lens 12, which is seated between an anterior capsule segment or anterior capsule 20 and a posterior capsular segment or posterior capsule 22. The anterior capsule 20 and the posterior capsule 22 meet at an equatorial region 23 of the lens capsule 18. The eye 10 also comprises an anterior chamber 24 located in front of the iris 16 and a posterior chamber 26 located between the iris 16 and the lens capsule 18.

A common technique of cataract surgery is extracapsular cataract extraction ("ECCE"), which involves the creation of an incision near the outer edge of the cornea 14 and an opening in the anterior capsule 20 (i.e., an anterior capsulotomy) through which the opacified lens 12 is removed. The lens 12 can be removed by various known methods including phacoemulsification, in which ultrasonic energy is applied to the lens to break it into small pieces that are promptly aspirated from the lens capsule 18. Thus, with the exception of the portion of the anterior capsule 20 that is removed in order to gain access to the lens 12, the lens capsule 18 remains substantially intact throughout an ECCE. The intact posterior capsule 22 provides a support for the IOL and acts as a barrier to the vitreous humor within the posterior chamber 26. Following removal of the opacified lens 12, an artificial IOL is typically implanted within the lens capsule 18 through the opening in the anterior capsule 20 to mimic the transparency and refractive function of a healthy lens. The IOL may be acted on by the zonular forces exerted by a ciliary body 28 and attached zonules 30 surrounding the periphery of the lens capsule 18. The ciliary body 28 and the zonules 30 anchor the lens capsule 18 in place and facilitate accommodation, the process by which the eye 10 changes optical power to maintain a clear focus on an image as its distance varies. In patients with damaged zonules from trauma or disease, the position of the lens capsule 18 can be unstable, which may result in deformations of the lens capsule, ineffective accommodation, difficult removal of the lens, and/or challenging implantation of an IOL.

A frequent complication of ECCE and other forms of cataract surgery is opacification of the posterior capsule 22. Posterior capsule opacification ("PCO") results from the migration of residual lens epithelial cells from the "equatorial" region of the lens toward the center of the posterior capsule 22. One factor contributing to the development of PCO is contact between the IOL and the surface of the posterior capsule 22. Subsequent to ECCE, the lens epithelial cells may proliferate between the IOL and the surface of the posterior capsule 22, leading to wrinkling and clouding of the normally clear posterior capsule 22. If clouding of the posterior lens capsule 22 occurs within the visual axis, then the patient will experience a decrease in visual acuity and may require additional surgery to correct the patient's vision.

A widely utilized procedure to clear the visual axis of PCO is Neodymium: Yttrium-Aluminum-Garnet ("Nd:YAG") laser capsulotomy, in which a laser beam is used to create an opening in the center of the cloudy posterior capsule. However, Nd:YAG laser capsulotomy exposes patients to the risk of severe complications that can lead to significant visual impairment or loss, such as retinal detachment, papillary block glaucoma, iris hemorrhage, uveitis/vitritis, and cystoid macula edema. Moreover, the laser energy is ordinarily directed though the IOL, which may damage the optics of the implant or disrupt its placement within the lens capsule. Also, a laser capsulotomy may compromise the accommodative ability of the lens implant. Accordingly, there exists a need to prevent the occurrence of PCO rather than treating PCO at a later date after implantation of an IOL. This is especially desirable for the new generation of IOLs (i.e., accommodating IOLs) that are capable of accommodating in response to ciliary body contraction and need an intact posterior capsule to optimally function.

The system and methods disclosed herein overcome one or more of the deficiencies of the prior art.

SUMMARY

In one exemplary aspect, the present disclosure is directed to an implantable capsule expander device. In one aspect, the present disclosure is directed to an implantable capsule expander device for insertion within a lens capsule of an eye of a patient. The implantable capsule expander device comprises an arcuate center portion, an outermost peripheral portion, and a receiving portion. In one aspect, the arcuate center portion includes first and second rims and has a first height. In one aspect, the outermost peripheral portion includes a second height that is less than the first height, wherein the center portion and the outermost peripheral portion are configured to stabilize the capsule expander device within the lens capsule and to expand the lens capsule. In one aspect, the receiving portion is sized to receive an artificial intraocular lens. In one aspect, the receiving portion is formed between the first and second rims.

In one aspect, the peripheral portion comprises a plurality of orifices spaced circumferentially around the peripheral portion.

In another exemplary aspect, the present disclosure is directed to a capsule expander system. In one aspect, the present disclosure is directed to a capsule expander system for inserting a capsule expander within a lens capsule of an eye of a patient. The capsule expander system comprises an annular capsule expander and a delivery instrument configured to position the capsule expander in the eye. In one aspect, the annular capsule expander is configured to stabilize within and to expand the lens capsule when in an expanded condition. In one aspect, the capsule expander comprises a circumferentially tapered profile wherein a center portion of the capsule expander includes a first height and an outermost peripheral portion of the capsule expander includes a second height that is less than the first height. In one aspect, the capsule expander comprises an outer, convex surface and an inner, concave surface. In one aspect, the inner surface includes an IOL engagement feature shaped and configured to stabilize and center an IOL within the capsule expander. In one aspect, the delivery instrument comprises a lumen with a longitudinal axis and a plunger longitudinally disposed in the lumen. In one aspect, the lumen is sized to receive the capsule expander in an unexpanded condition. In one aspect, the plunger is configured to translate longitudinally within the lumen to displace the capsule expander from the lumen.

In one aspect, the capsule expander comprises raised rim portions at the center portion that are angled away from the outermost peripheral portion and configured to contact the lens capsule.

In one aspect, the raised rim portions include a contact surface forming a right angle with the peripheral portion.

In another exemplary aspect, the present disclosure is directed to a method for stabilizing a lens capsule of an eye and inhibiting opacification of the lens capsule. In one aspect, the method comprises inserting a capsule expander in an unexpanded condition into a lumen of a delivery instrument sized to receive the capsule expander, wherein the capsule expander has a circumferentially tapered profile in an expanded condition, and wherein the delivery instrument comprises a plunger longitudinally disposed within a lumen. In one aspect, the method further comprises moving the plunger along the longitudinal axis of the lumen toward a distal end of the delivery instrument to displace the capsule expander from the lumen of the delivery instrument into the lens capsule and allow the capsule expander to assume the expanded condition. In one aspect, the method further comprises positioning the capsule expander against an equatorial region of the lens capsule such that the capsule expander is centered within the lens capsule and the capsule expander separates an anterior capsule and a posterior capsule of the lens capsule.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 2b illustrates a side view of the exemplary capsule expander device shown in FIG. 2a.

FIG. 4 illustrates a top plan view of the exemplary capsule expander device shown in FIG. 2a.

FIG. 5 illustrates a cross-sectional side view of the exemplary capsule expander device shown in FIG. 2a.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for use in inhibiting and/or alleviating medical conditions, including ophthalmic conditions such as posterior capsular opacification ("PCO"), anterior capsular opacification ("ACO"), and destabilization of the lens capsule. In some instances, embodiments of the present disclosure comprise capsule expander devices configured to reduce the occurrence of ACO and/or PCO after lens extraction by inhibiting migration of lens epithelial cells after extraction of an opacified lens and before insertion of an intraocular lens implant ("IOL"). In some instances, embodiments of the present disclosure comprise capsule expander devices configured to stabilize the lens capsule 18 within the posterior chamber of an eye during and after intraocular surgery. In some instances, the capsule expander devices described herein facilitate efficient removal, exchange, and/or replacement of IOLs.

In exemplary embodiments disclosed herein, the capsule expander device comprises an annular and flexible ring configured to expand the lens capsule 18 when implanted in the lens capsule and to prevent the anterior capsule 20 from touching the posterior capsule 22 and, consequently, minimize proliferation of the lens epithelial cells from the equatorial region over the surface of the anterior capsule 20 and posterior capsule 22. In some embodiments, the capsule expander device comprises square anterior and posterior edges configured to abut the lens capsule 18 and inhibit proliferation of the lens epithelial cells across the surface of the anterior capsule 20 and posterior capsule 22.

In some embodiments, the capsule expander device is configured to receive and seat an IOL, and may include a circular groove configured to receive the haptics of an IOL and/or additional intraocular devices. In some instances, the capsule expander may prevent the IOL from contacting either the anterior capsule 20 or the posterior capsule 22. In some embodiments, the IOL may be inserted into the eye during an ophthalmic procedure through the same incision that was used to insert the capsule expander device. In addition, the capsule expander device comprises peripheral holes spaced around the ring that allow aqueous humor to circulate effectively through the device, around the IOL, and within the lens capsule 18.

In one exemplary aspect, the present disclosure provides a capsule expander device having shape memory characteristics. The capsule expander device may assume an unexpanded condition to facilitate atraumatic insertion into and removal from an eye through a primary incision, and can assume a predetermined, expanded condition within the eye. In one embodiment, in its expanded condition, the capsule expander device comprises a substantially circular toroid or ring. In some embodiments, the capsule expander device comprises a ring that tapers toward its periphery to facilitate stabilization of the capsule expander device inside the lens capsule 18. This may allow the capsule expander device to be self-stabilized and self-retained in the eye (i.e., without the use of sutures, tacks, or a manually held instrument). Thus, the capsule expander devices, systems, and methods disclosed herein stabilize the lens capsule within the posterior chamber and prophylactically treat capsular opacification without inadvertently damaging the lens capsule 18 or other ocular cells.

Figure 2A:
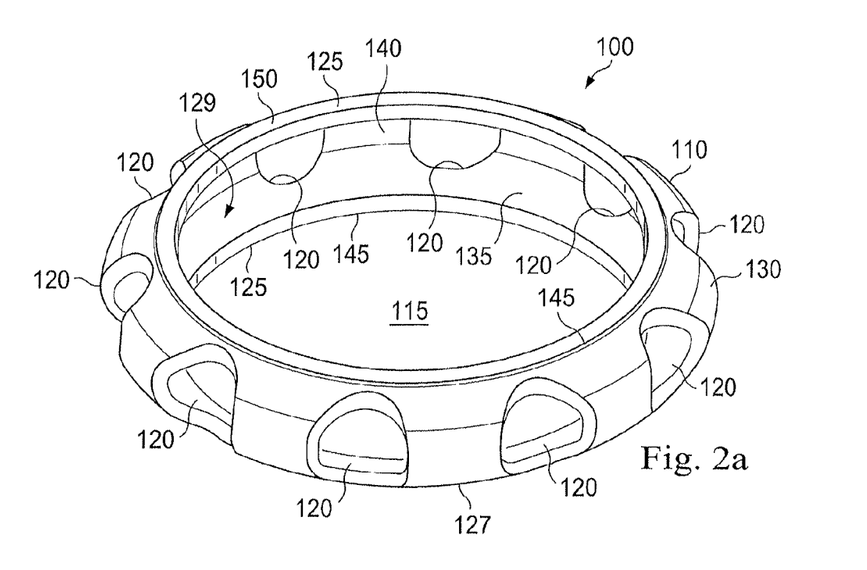
FIG. 2a illustrates a perspective view of an exemplary capsule expander device according to one embodiment consistent with the principles of the present disclosure.

FIG. 2a illustrates a capsule expander device 100 in an expanded condition according to one exemplary embodiment of the present disclosure. Though the capsule expander device 100 shown in FIG. 2a is configured for use in the eye, the capsule expander device may be used in other anatomical systems, including by way of non-limiting example, the gastrointestinal system, the respiratory system, and the cardiovascular system. The capsule expander device 100 comprises a flexible support member 110 having a central opening 115. The capsule expander device 100 includes a plurality of orifices 120 disposed circumferentially on the periphery of the support member 110. In the pictured embodiment, the capsule expander device 100 comprises two raised rim portions 125 extending integrally from the support member 110. For simplicity of description, it should be understood that, in this embodiment, the raised rim portions are substantially identical, except for the differences described herein.

The support member 110 comprises an annular ring with a substantially circular shape configured to match the substantially circular cross-sectional shape of the lens capsule 18 (shown in FIG. 1) when the lens capsule is divided on a coronal plane through the equatorial region 23. The support member 110 is shaped and configured to maintain the natural circular contour of the lens capsule 18 and to stabilize the lens capsule in the presence of compromised zonular integrity when the capsule expander device 100 is positioned in the eye. In the pictured embodiment, the support member 110 tapers from the rim portions 125 towards a peripheral portion 127. The peripheral portion 127 comprises the outermost circumferential region of the capsule expander device 100. In some embodiments, the angle of the taper from the rim portions 125 towards the peripheral portion 127 is selected to substantially match the angle of the equatorial region 23 in the lens capsule 18, thereby facilitating self-stabilization of the capsule expander device 100 within the eye.

The capsule expander device 100 is shaped and configured to expand the lens capsule 18, preventing the anterior capsule 20 from contacting the posterior capsule 22 and allowing the free circulation of aqueous humor within the lens capsule, both of which may inhibit lens epithelial cell proliferation. The support member 110 includes an outer surface 130 and an inner surface 135. The outer surface 130 is curved outward and convex, and the inner surface 135 is concave. The angles of curvature of the inner surface 135 substantially match the angles of curvature of the outer surface 130. In some embodiments, the outer surface 130 (and, in particular, the peripheral portion 127) is shaped and contoured to substantially match the curvature of the inner surface of the lens capsule 18 near the equatorial region 23 (shown in FIG. 1), thereby facilitating self-stabilization of the capsule expander device 100 within the eye. The concave shape of the inner surface 135 is a receiving portion 129 that may receive edges or portions of an IOL or its haptics. In some embodiments, the outer surface 130 is configured to conform against the inner surface of the lens capsule 18 near the equatorial region 23.

In the pictured embodiment, the concave receiving portion 129 includes an IOL engagement feature 140 on the inner surface 135. The IOL engagement feature 140 is shaped and sized to receive and accommodate an IOL, and, in some embodiments, the haptics of an IOL. In the pictured embodiment, the IOL engagement feature 140 comprises a groove extending circumferentially along the inner surface 135. The IOL engagement feature 140 is shaped as a ring-shaped indentation extending around the inner surface 135. In other embodiments, the support member 110 may include any number, type, and arrangement of IOL engagement features. For example, the IOL engagement feature may comprise any of a variety of engagement features, including without limitation, a protrusion, a depression, hooks, loops, detents, snap-fit members, and/or adhesive. In some embodiments, the IOL engagement feature is shaped and sized to receive and accommodate multiple IOLs and/or other intraocular devices. In this regard, some embodiments may include multiple IOL engagement features. The IOL engagement feature 140 is described further below in relation to FIGS. 5 and 6.

Figure 2B:
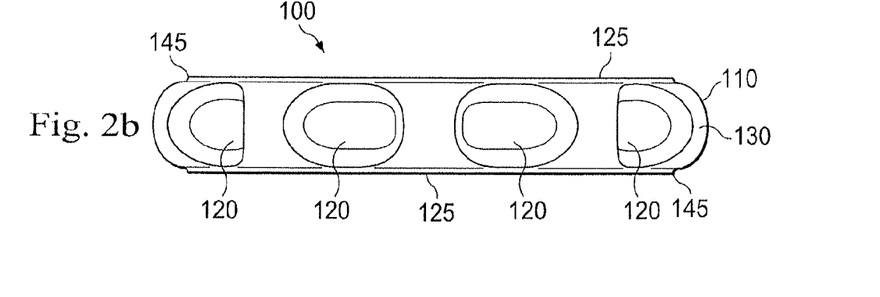

The structure of the capsule expander device 100, including the central opening 115 and the orifices 120, allow the free circulation of aqueous humor within the lens capsule, which may inhibit lens epithelial cell proliferation. In the pictured embodiment shown in FIG. 2a, the support member 110 includes ten orifices 120 arranged in a symmetrical pattern around the support member. As shown in FIGS. 2a and 2b, the orifices 120 are evenly spaced apart along the support member 110. The orifices 120 are shaped, sized, and positioned around the support member 110 to facilitate the flow of aqueous humor through the capsule expander device 100. In the pictured embodiment, the orifices 120 are shaped as generally ovoid or oblong holes through the periphery of the support member 110. In other embodiments, the capsule expander device may include any shape, number, and arrangement of orifices that allow for adequate flow of aqueous humor through the capsule expander device. For example, in some embodiments, the orifices may have a generally circular shape. In the pictured embodiment, the orifices 120 consist of single, large holes. In some embodiments, the orifices may have an oblong shape (e.g., as seen in FIG. 3h). In other embodiments, the orifices may consist of multiple, small holes forming a mesh-like configuration (e.g., see FIG. 3i). In some embodiments, the orifices may be unevenly spaced apart along the support member 110. The number and arrangement of the orifices 120 may be selected in consideration of, among other factors, the type of condition to be treated, the patient's particular anatomy, or the type of IOL to be placed within the capsule expander device. The orifices 120 lower the overall volume of the capsule expander device 100. In some embodiments, the orifices 120 increase the flexibility, contractibility, and expandability of the capsule expander device 100.

As shown in FIGS. 2a and 2b, the two raised rim portions 125 (e.g., an anterior and a posterior raised rim portion) extending integrally from the support member 110 comprise square anterior and posterior edges 145. The edges 145 form right angles or near-right angles to the support member 110. The rim portions 125 are shaped and configured to create circumferential, 360 degree barriers to the proliferation and migration of lens epithelial cells across the lens capsule 18 (shown in FIG. 1) past the rim portions. In some embodiments, the rim portions 125 are shaped and configured to create circumferential, 360 degree barriers to the proliferation and migration of lens epithelial cells across the anterior capsule 20 (shown in FIG. 1) past the rim portions, thereby inhibiting ACO. In some embodiments, the rim portions 125 are shaped and configured to create circumferential, 360 degree barriers to the proliferation and migration of lens epithelial cells across the posterior capsule 22 (shown in FIG. 1) past the rim portions, thereby inhibiting PCO. In some embodiments, the rim portions 125 are shaped and configured to create circumferential, 360 degree barriers to the proliferation and migration of lens epithelial cells across the anterior capsule 20 and posterior capsule 22 (shown in FIG. 1) past the rim portions, thereby inhibiting both ACO and PCO.

As shown in FIG. 2a, the rim portions 125 also comprise anterior and posterior contact surfaces 150, which are shaped and configured to contact the inner surfaces of the anterior and posterior lens capsules 20, 22. In the pictured embodiment, the contact surfaces 150 are substantially flat. In various embodiments, the contact surfaces 150 may have any of a variety of shapes designed to engage the inner surfaces of the anterior lens capsule 20 and the posterior lens capsule 22 to block the proliferation and migration of lens epithelial cells across the lens capsule 18, including without limitation, a curved surface. In some embodiments, the contact surface has a curvature substantially corresponding to the curvature of the inner surface of the lens capsule 18 where the rim portion is designed to contact the lens capsule. In the pictured embodiment, the contact surface 150 is substantially smooth. In other embodiments, the contact surface may be textured.

Figure 3A:
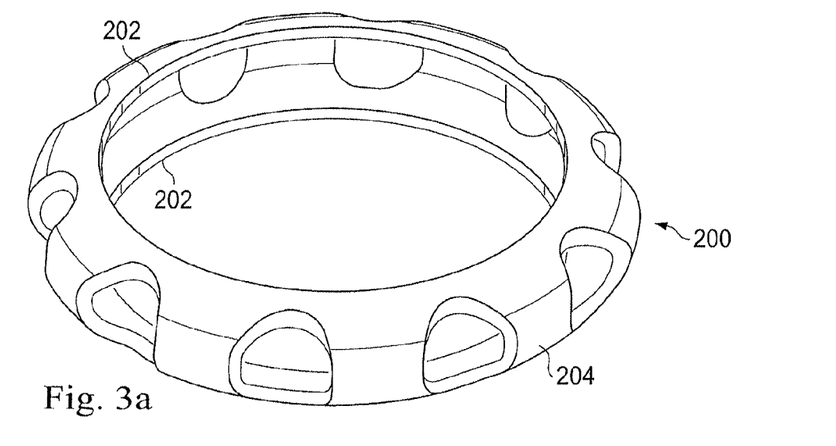
FIG. 3a illustrates a perspective view of an exemplary capsule expander device according to another embodiment consistent with the principles of the present disclosure.

As shown in FIG. 3a, some embodiments may lack raised rim portions 125. A capsule expander device 200 shown in FIG. 3a is substantially similar to the capsule expander device 100 except for the differences noted herein. Namely, the capsule expander device 200 lacks the raised rim portions 125. The capsule expander device 200 includes anterior and posterior rims or edges 202 that define the inner perimeter of a support member 204. The edges 202 are not substantially raised from the outer surface of the capsule expander device 200. In the pictured embodiment, the edges 202 are sharply angled from the remainder of the support member 204, and may form barriers (e.g., squared-edged or 90 degree barriers) to the migration of lens epithelial cells past the edges 202.

Figure 3B:
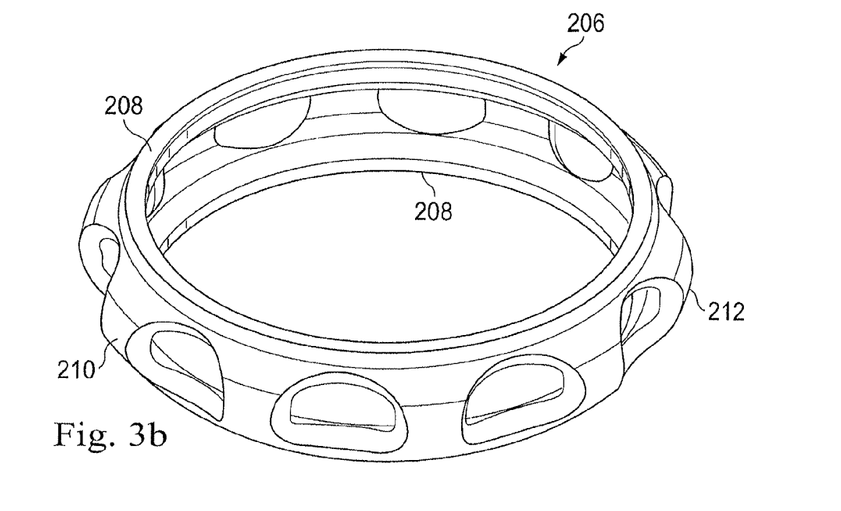
FIG. 3b illustrates a perspective view of an exemplary capsule expander device according to another embodiment consistent with the principles of the present disclosure.
Figure 3C:
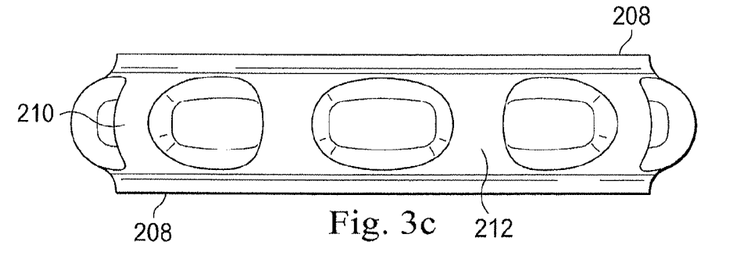
FIG. 3c illustrates a side view of the exemplary capsule expander device shown in FIG. 3b.
Figure 3D:
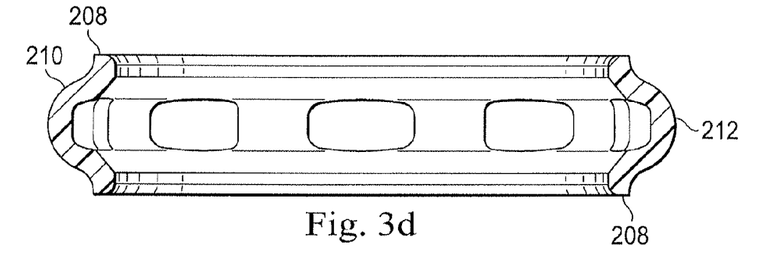
FIG. 3d illustrates a cross-sectional side view of the exemplary capsule expander device shown in FIG. 3b.

In other embodiments, the edges may be rounded or found at other angles relative to the outer surface. For example, in FIGS. 3b-3d, a capsule expander device 206 is shown that is substantially similar to the capsule expander device 100 except for the differences noted herein. Namely, the capsule expander device 206 lacks the raised rim portions 125, and instead includes anterior and posterior rims or edges 208 that define the inner perimeter of a support member 210. The edges 208 are more raised from an outer surface 212 of the capsule expander device 206 than the raised rim portions 125 are raised from the outer surface 130 of the capsule expander device 100. As better shown in FIG. 3c, the edges 208 gently slope away from and are gradually angled from the remainder of the support member 210, and form barriers (e.g., squared-edged or 90 degree barriers) to the migration of lens epithelial cells past the edges 208.

Figure 3E:
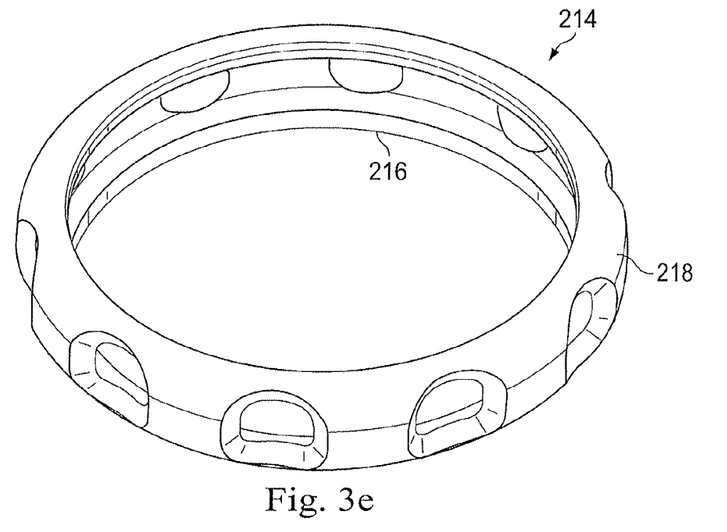
FIG. 3e illustrates a perspective view of an exemplary capsule expander device according to another embodiment consistent with the principles of the present disclosure.
Figure 3F:
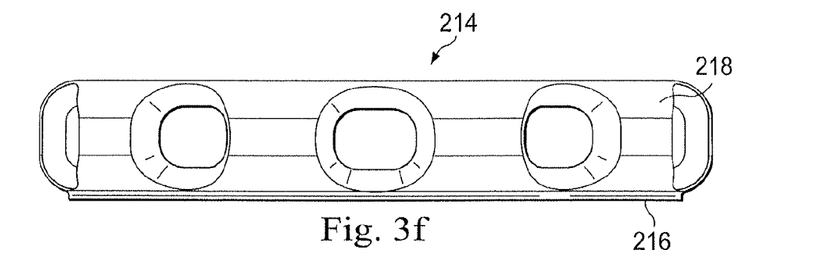
FIG. 3f illustrates a side view of the exemplary capsule expander device shown in FIG. 3e.
Figure 3G:
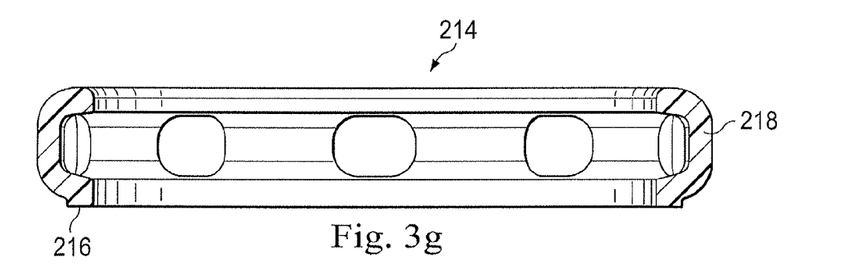
FIG. 3g illustrates a cross-sectional side view of the exemplary capsule expander device shown in FIG. 3e.
Figure 3H:
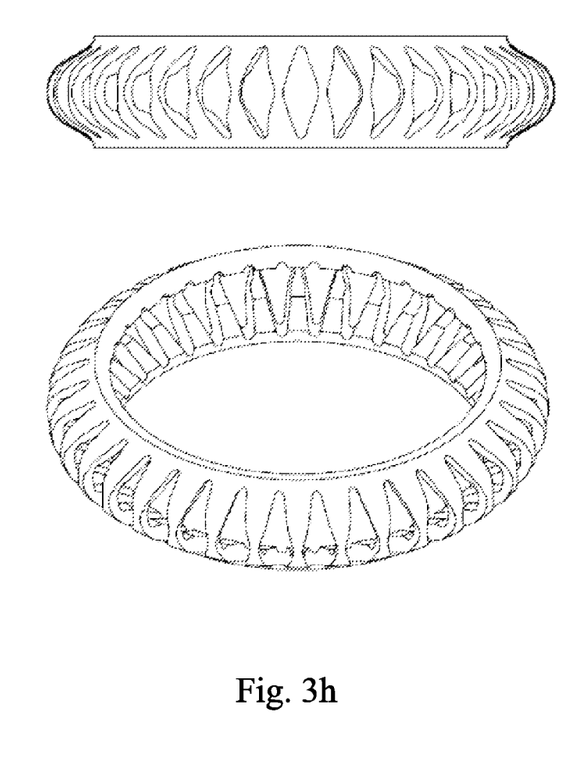
FIG. 3h illustrates two views of an exemplary capsule expander device with oblong holes.
Figure 3I:
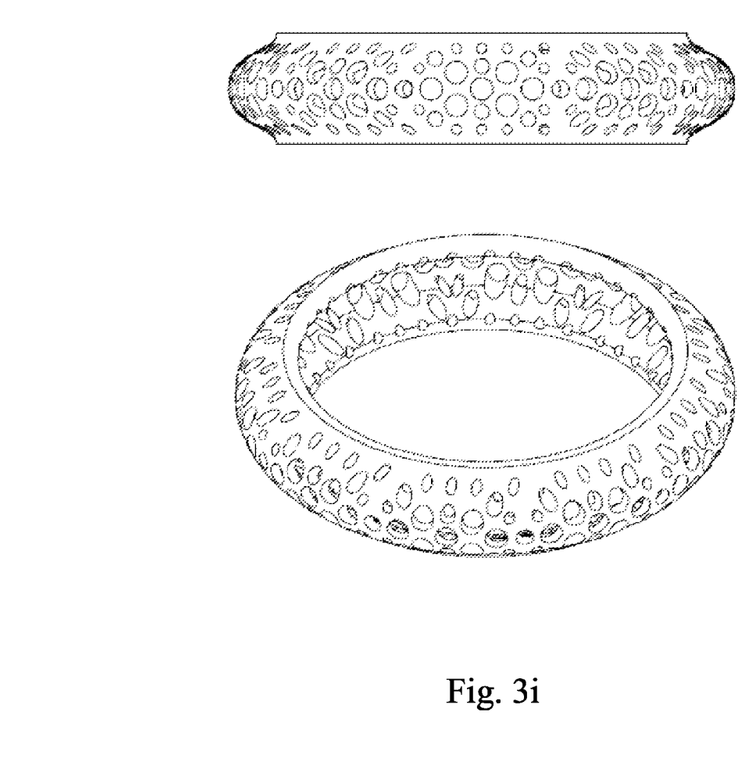
FIG. 3i illustrates two views of an exemplary capsule expander device with mesh style holes.

In FIGS. 3e-3g, a capsule expander device 214 is shown that is substantially similar to the capsule expander device 100 except for the differences noted herein. Namely, the capsule expander device 214 lacks the anterior raised rim portion 125, and instead includes only a posterior rim or edge 216 that defines the inner, posterior perimeter of a support member 218. The edge 216 is substantially similar to the posterior raised rim portion 125 of the capsule expander device 100. As better shown in FIGS. 3f and 3g, the edge 216 is sharply angled from the remainder of the support member 218, and forms a barrier (e.g., squared-edged or 90 degree barrier) to the migration of lens epithelial cells on the posterior capsular surface past the edge 216.

Figure 4:
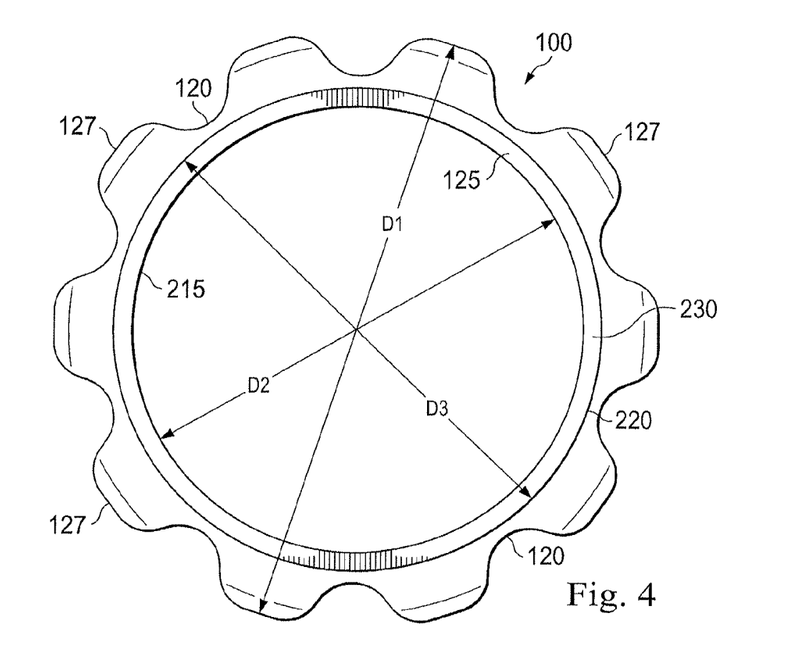

As shown in FIG. 4, the support member 110 is sized to provide adequate stabilization of the capsule expander device 100 in an expanded condition within the lens capsule while remaining small enough to limit interference with other surgical instruments and/or a surgeon's hand during an ophthalmological procedure. In one embodiment, the support member 110 has an external diameter D1 of 10 mm. In other embodiments, the support member 110 may have an external diameter D1 ranging from, for example only, approximately 6 to 11 mm in an expanded condition. Other diameter ranges are contemplated.

The support member 110 is also sized to provide adequate stabilization of the IOL in an expanded condition within the central opening 115 of the capsule expander device 100 in an expanded condition. The internal diameter D2 partially extends across the central opening 115, spanning the distance from one side of an inner margin 215 of the raised rim portion 125 to the opposite side of the inner margin 215 of the raised rim portion 125. In one embodiment, the support member 110 has an internal diameter D2 of 7.5 mm. In other embodiments, the support member 110 may have an internal diameter D2 ranging from, for example only, approximately 6 to 10.8 mm in an expanded condition.

The support member 110 includes a diameter D3 that extends from one side of an outer margin 220 of the raised rim portion 125 to the opposite side of the outer margin 220 of the raised rim portion 125. The diameter D3 extends across an arcuate center portion 230 of the support member 110. In one embodiment, the support member 110 has an internal diameter D3 of 8.1 mm. In other embodiments, the support member 110 may have an internal diameter D3 ranging from, for example only, approximately 6 to 11 mm in an expanded condition. Thus, in some embodiments, the internal diameter D3 may equal the external diameter D1, allowing the outer surface 130 of the support member 110 to be a substantially straight wall.

Figure 5:
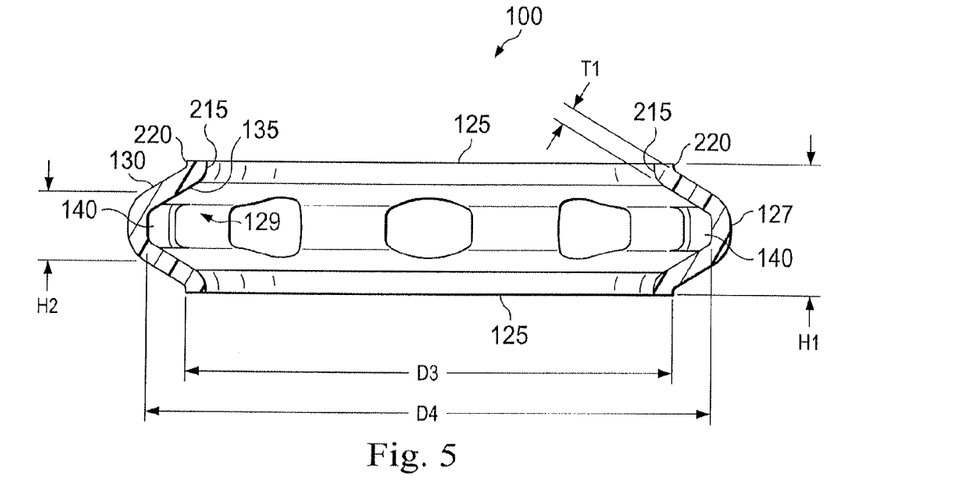

As shown in FIG. 5, the support member 110 includes an internal diameter D4 that extends across the central opening 115 when the capsule expander device is an expanded condition, spanning the distance from one side of the IOL engagement feature 140 to the opposite side of the IOL engagement feature 140. In embodiments having more than one IOL engagement feature, or a discontinuous IOL engagement feature, the internal diameter D4 extends across the central opening 115, spanning the distance from one IOL engagement feature to either an IOL engagement feature on the opposite side of the inner surface 135. In embodiments lacking an IOL engagement feature, the internal diameter D4 extends from one side of the inner surface 135 to a directly opposite side of the inner surface 135. In one embodiment, the support member 110 has an internal diameter D4 of 9.5 mm. In other embodiments, the support member 110 may have an internal diameter D4 ranging from, for example only, approximately 6.5 to 11.5 mm in an expanded condition.

The capsule expander device 100 includes a height H1 extending between the outer surfaces of the raised rim portions 125 when the capsule expander device is in an expanded condition. In one embodiment, the capsule expander device has a height H1 of 2.2 mm. In other embodiments, the capsule expander device 100 may have a height H1 ranging from, for example only, approximately 0.5 to 3 mm in an expanded condition. Other heights are contemplated.

The capsule expander device 100 includes a height H2 extending between the outer surfaces of the peripheral portion 127 when the capsule expander device is in an expanded condition. In one embodiment, the capsule expander device has a height H2 of 1.253 mm. In other embodiments, the capsule expander device 100 may have a height H2 ranging from, for example only, approximately 0.1 to 3 mm in an expanded condition. Other heights are contemplated.

The raised rim portions 125 of the capsule expander device 100 include a thickness T1 extending from the outer surface 130 to the inner surface 135 of the raised rim portions. In one embodiment, each raised rim portion 125 has a thickness T1 of 0.32 mm. In other embodiments, each raised rim portion 125 may have a thickness T1 ranging from, for example only, approximately 0.1 to 0.5 mm in an expanded condition. Other thicknesses are contemplated. Although the raised rim portions 125 of the capsule expander device 100 are substantially identical in size and cross-sectional shape, other embodiments may include raised rim portions of varying sizes and shapes (e.g., where the anterior raised rim portion is different from the posterior raised rim portion).

The capsule expander device 100 is shaped and configured to enable insertion through a small incision into the eye 10 as well as self-stabilization within the lens capsule 18 (shown in FIG. 1). In some embodiments, the capsule expander device is shaped and configured to be insertable in an unexpanded condition through an incision less than 2.4 mm in diameter. The capsule expander device 100 is expandable from an unexpanded condition to an expanded condition having a predetermined shape configuration. For example, in the embodiment pictured in FIG. 2a, the capsule expander device 100, in an expanded condition, comprises a continuous, closed, annular ring with a predetermined circular shape that substantially corresponds to the shape of an average human lens capsule (i.e., the cross-sectional shape of the center of an average human lens capsule on coronal section). In other embodiments, the capsule expander device may have any of a variety of predetermined shapes in the expanded condition, including, by way of non-limiting example, an oval, an oblong, or an elliptical shape. In other embodiments, the capsule expander device comprises an open ring or a C-shaped ring.

The capsule expander device 100 is constructed from a structurally deformable biocompatible material that can elastically or plastically deform without compromising its integrity. The capsule expander device 100 may be made from a self-expanding biocompatible material, such as Nitinol or a resilient polymer such as AcrySof or silicone, or an elastically compressed spring temper biocompatible material. Other materials having shape memory characteristics, such as particular metal alloys, may also be used. The shape memory materials allow the support member to be restrained in a low profile configuration during delivery into the eye and to resume and maintain its expanded shape in vivo after the delivery process. The material composition of the capsule expander device 100 resiliently biases the capsule expander device 100 toward the expanded condition. In particular, in this example, the capsule expander device 100 is formed of an elastic material allowing the capsule expander device to elastically deform to an unexpanded state to facilitate delivery through small incision (e.g., through a tubular delivery instrument), and spring back to an expanded state as it enters the eye. In other embodiments, the capsule expander device is made of a shape memory alloy having a memory shape in the expanded configuration. In some embodiments, the capsule expander is made of a material that is stiffer at room temperature and expands gradually as it is exposed to body temperature.

The capsule expander device may be formed from any of a variety of biocompatible materials having the requisite properties of resilience, flexibility, expandability, and suitability for use in intraocular procedures. In some embodiments, the individual components of the capsule expander device 100, including the support member 110 and the raised rim portions 125, may be formed of different biocompatible materials of varying degrees of pliancy. For example, in some embodiments, the support member 110 may be formed of a more flexible and pliant material than the raised rim portions 125 to minimize contact damage or trauma to the surface of the lens capsule 18. In other embodiments, the reverse relationship may exist. The capsule expander device 100 may be coated with any of a variety of biocompatible materials, including, by way of non-limiting example, polytetrafluoroethylene (PTFE).

The capsule expander device 100 may be shaped and configured to be transparent enough to provide for visualization through it to observe, by way of non-limiting example, underlying tissue, vessels, air bubbles, and/or bleeding. In some embodiments, the support member 110 and/or the raised rim portions 125 may be semi-transparent or opaque so as to be clearly visible during ophthalmic procedures.

Figure 6:
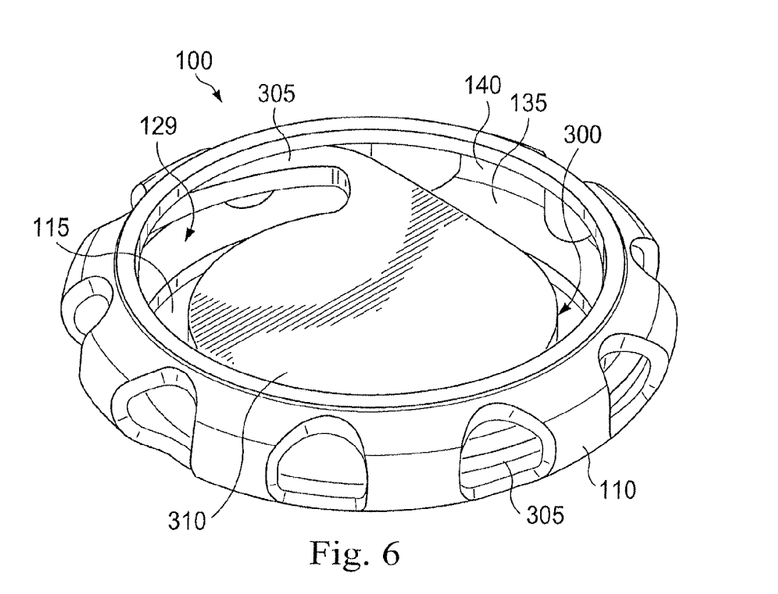
FIG. 6 illustrates a perspective view of an exemplary IOL seated within the exemplary capsule expander device shown in FIG. 2a according to one embodiment consistent with the principles of the present disclosure.

FIG. 6 illustrates a perspective view of the capsule expander device 100 containing an exemplary IOL 300 within the central opening 115 of the support member 110. The IOL 300 is self-retained within the capsule expander device 100. In particular, the IOL 300 includes haptics 305, which are shaped and configured to removably anchor the IOL 300 within the concave receiving portion 129 of the capsule expander device 100. The haptics 305 comprise substantially pliable, curved, elongate members extending outwardly from a body 310 of the IOL 300. The haptics 305 are shaped and configured to expand into the IOL engagement feature 140 on the inner surface 135 of the support member 110. As mentioned above, the IOL engagement feature 140 in the pictured embodiment comprises a groove extending circumferentially along the inner surface 135. In some embodiments, the IOL engagement feature 140 is shaped and configured to receive and removably secure the haptics 305 of the IOL 300. In some embodiments, depending upon the shape of the IOL 300, the IOL 300 is received and removably secured within the capsule expander device 100 such that the IOL 300 will not contact either the anterior capsule 20 or the posterior capsule 22 (as seen in FIG. 1) when implanted within the eye. By keeping the lens capsule 18 open and expanded and out of direct contact with the IOL, the capsule expander device 100 allows the IOL 300 to be more easily implanted, as well as more easily explanted. Therefore, the capsule expander device 100 may facilitate lens replacement or exchange if necessary to treat the patient (either during or after the present ophthalmological procedure).

Figure 7:
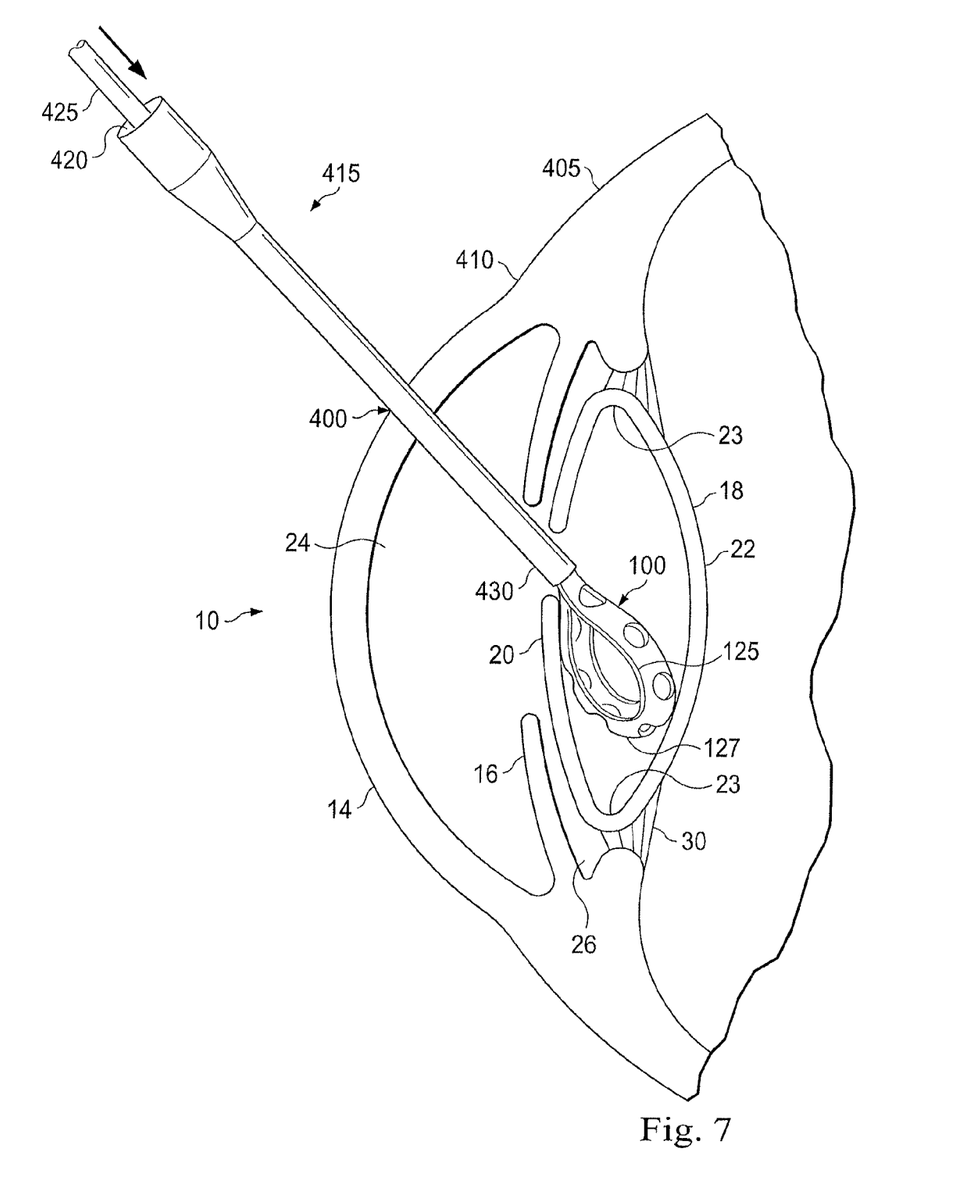
FIG. 7 illustrates a side view of the exemplary capsule expander device shown in FIG. 2a being ejected from an exemplary delivery instrument and inserted into an eye according to one exemplary embodiment of the present disclosure.
Figure 8:
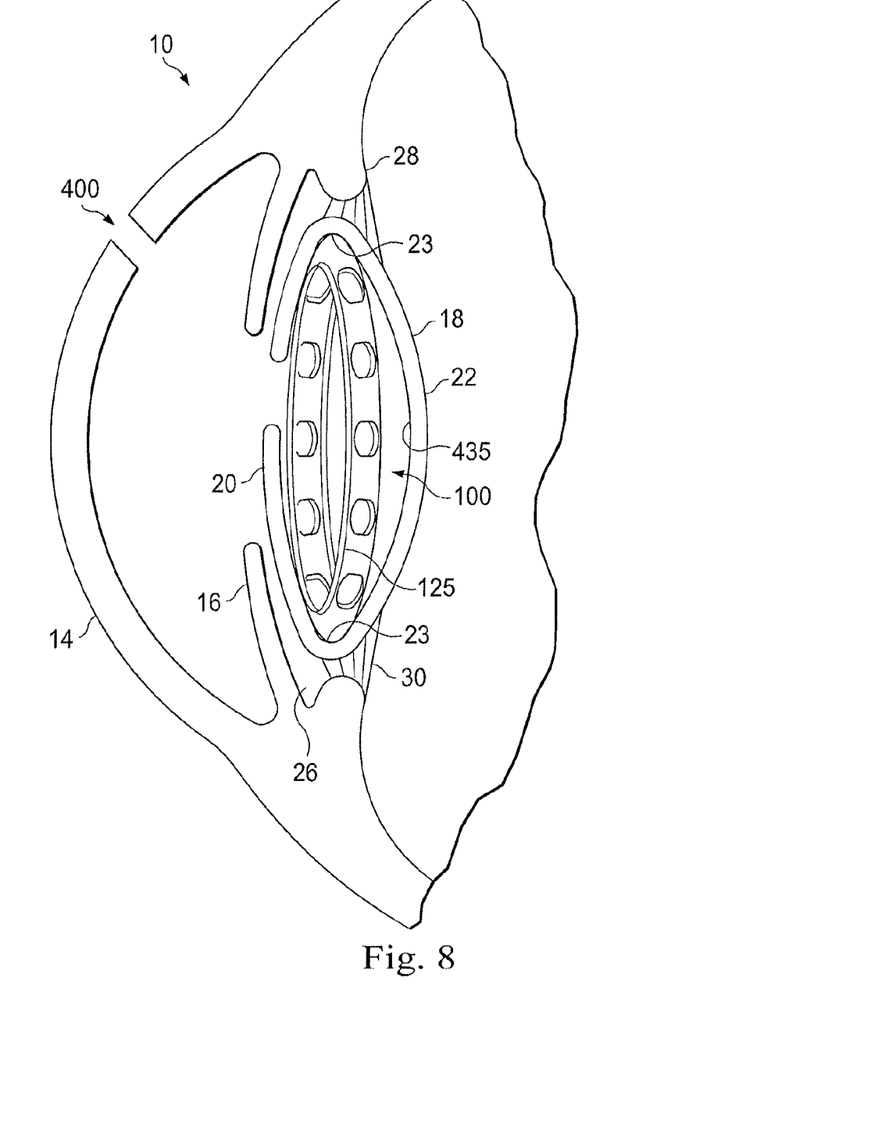
FIG. 8 illustrates a side view of the capsule expander device shown in FIG. 2a positioned within an eye according to the principles of the present disclosure.
Figure 9:
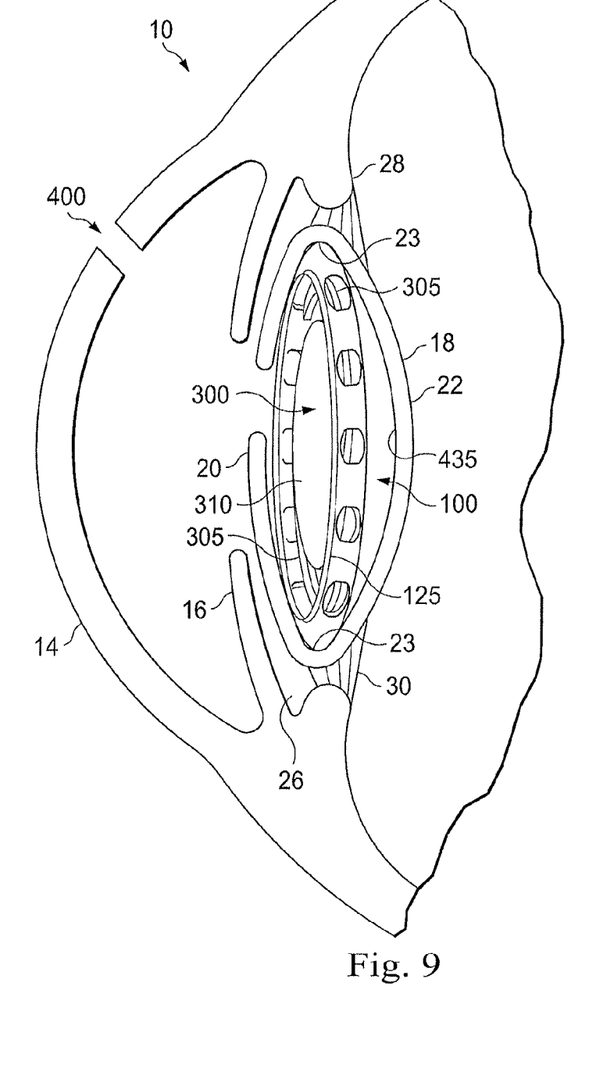
FIG. 9 illustrates a side view of the exemplary IOL shown in FIG. 6 seated within the capsule expander device shown in FIG. 2a, which is positioned within an eye according to the principles of the present disclosure.

FIGS. 7-9 show a method of inserting and positioning the capsule expander device 100 in the lens capsule 18 of the eye 10 to expand the lens capsule 18 and retain the IOL 300 according to one embodiment of the present disclosure. For the sake of simplicity, the lens capsule 18 is shown post-anterior capsulotomy (i.e., after a portion of the anterior capsule 20 has been removed to facilitate removal of the natural lens and/or insertion of the capsule expander device 100 and, in some instances, the IOL 300).

With reference to FIG. 7, after a 1.8-4 mm incision 400 is made in the cornea 14, the anterior chamber 24 is filled in a conventional manner with a viscoelastic fluid to prevent the cornea 14 from collapsing and to provide lubrication and support for the subsequent insertion of surgical instruments. In some instances, the incision 400 comprises a clear corneal incision. In other instances, the incision 400 may be made in a sclera 405 or a limbus 410. In some instances, the incision 400 may be the same incision through which the native lens had been removed from the eye 10. A delivery instrument 415 having a longitudinal axis is inserted through the incision 400, through the anterior chamber 24, and into the posterior chamber 26. The delivery instrument 415 includes a lumen 420 sized to receive the capsule expander device 100 in an unexpanded condition and has an outer diameter sized to easily pass through the incision 400. The delivery instrument 415 includes a plunger 425 longitudinally disposed within the lumen 420, and the plunger is configured to translate longitudinally within the lumen to displace the capsule expander device 100 from the lumen.

As shown in FIG. 7, as the capsule expander device 100 is passed through the lumen 420 of the delivery instrument 415, the capsule expander device 100 is in an unexpanded condition. In particular, the support member 110 is in an unexpanded condition. In some embodiments, the capsule expander device 100 is delivered into the eye 10 after the removal of the native lens and/or a previously-implanted IOL through the incision 400, and the delivery instrument 415 is the same instrument used to remove the native lens and/or an IOL. In other embodiments, the delivery instrument 415 is a different instrument than the one used to remove the lens and/or the previously-implanted IOL. In one exemplary method, the user may advance the capsule expander device 100 from the delivery instrument 415 by advancing the plunger 425 in the direction of the arrow in FIG. 5 through the lumen 420 to push the capsule expander device 100 into the eye 10.

As shown in FIG. 7, as the capsule expander device 100 emerges from a distal end 430 of the delivery instrument 415, the capsule expander device 100 transitions from the unexpanded configuration into an expanded configuration having a substantially circular shape. In some embodiments, the user may direct the capsule expander device 100 within the eye 10 toward the equatorial region 23 of the lens capsule 18, which comprises the junction between the anterior capsule 20 and the posterior capsule 22. In one exemplary method, the user may advance the capsule expander device 100 into the lens capsule 18 to engage the peripheral portion 127 of the support member 110 against the equatorial region 23.

As shown in FIGS. 7 and 8, after the peripheral portion 127 of the support member 110 engages against the equatorial region 23, the user may advance the remainder of the capsule expander device 100 from the delivery instrument 415 into the lens capsule 18 of the eye 10. The plunger 425 may be utilized to manipulate the capsule expander device 100 to securely position the capsule expander device within the equatorial region 23 of the eye 10.

FIG. 8 illustrates the capsule expander device 100 positioned within the lens capsule 18 to expand the lens capsule in a substantially circular shape that mimics the original anatomic shape of the lens capsule. The capsule expander device 100 can maintain the lens capsule 18 in an expanded condition to separate the anterior capsule 20 from the posterior capsule 22. In some embodiments, the support member 110 may apply a compressive force against an inner surface of the lens capsule 18 at the equatorial region 23, thereby stabilizing the capsule expander device 100 against the inner surface of the lens capsule. The capsule expander device 100 is positioned within the lens capsule 18 such that the raised rim portions 125 of the capsule expander device contact the anterior capsule 20 and the posterior capsule 22 to inhibit the proliferation of lens epithelial cells from the equatorial region 23. The capsule expander device 100 is positioned such that it does not obstruct the visual axis.

As illustrated in FIG. 8, the capsule expander device 100 is configured to provide excellent self-retention within the eye, thereby allowing instrument-free use of the capsule expander device 100. In other words, separate devices for holding the capsule expander device 100 in place within the lens capsule 18 are not required. In some embodiments, the capsule expander device 100 self-centers within the lens capsule 18 as it is nestled into the equatorial region 23. The self-retaining nature of the capsule expander device 100, provided by the shape and contour of the support member 110, eliminates the need for suturing or holding of the capsule expander device 100.

After the capsule expander device 100 has been implanted into the eye 10, a surgeon can then implant an IOL (e.g., the IOL 300 shown in FIG. 6) through the same incision 400 used to insert the capsule expander device 100 and maneuver the IOL to lie within the capsule expander device 100 as described above in relation to FIG. 6. In some embodiments, the IOL is delivered into the eye 10 after the capsule expander device 100 is delivered into the eye 10 through the incision 400, and the delivery instrument used is the same delivery instrument 415 used to deliver the capsule expander device 100 into the eye 10 immediately prior to the insertion of the IOL. In other embodiments, the delivery instrument is a different delivery instrument than the one used to deliver the capsule expander device 100.

In some embodiments, the IOL may be inserted into the eye 10 along with the capsule expander device. For example, in some embodiments, the IOL and the capsule expander device may be preloaded into a single cartridge such that they emerge from the delivery instrument together and already associated together.

FIG. 9 illustrates the IOL 300 positioned within the capsule expander device 100, which is securely positioned within the lens capsule 18. As shown in FIG. 9, the haptics 305 are positioned against IOL engagement feature 140, thereby stabilizing the IOL 300 within the capsule expander device 100 and inside the eye 10 without the need for sutures or staples. The haptics 305 may aid in centering the IOL 300 within the capsule expander device 100. The capsule expander device 100, which is securely positioned centrally within the lens capsule 18, aids in centering the IOL 300 within the lens capsule or capsular bag.

In some instances, the lens capsule 18 may mold or shape an IOL and structurally contribute to control the refraction of the IOL. As mentioned above, the IOL may be acted on by the zonular forces exerted by the zonules 30 and the ciliary body 28 surrounding the periphery of the lens capsule 18. The ciliary body 28 and the zonules 30 anchor the IOL 300 in place and facilitate accommodation, the process by which the eye 10 changes optical power to maintain a clear focus on an image as its distance varies. The capsule expander device 100 may stabilize and re-center the lens capsule 18 within the posterior chamber, thereby increasing the functionality and stability of the zonules 30 and/or the ciliary body 28. Thus, the devices, systems, and methods described herein may supply a receptive environment for accommodative IOLs (e.g., IOLs that are configured to change focus and accommodate vision) by inhibiting ACO and PCO without sacrificing capsular compliance or integrity. Moreover, embodiments in accordance with the present disclosure facilitate the insertion and/or removal of an IOL from the lens capsule 18 by providing a stable environment for the IOL that prevents the IOL from contacting the inner surface 430 of the lens capsule.

Embodiments in accordance with the present disclosure provide users with an atraumatic tool to block the proliferation and migration of lens epithelial cells across the inner surface 435 of the lens capsule 18 (i.e., the inner surfaces of both the anterior and posterior capsules) and prophylactically treat PCO to provide a stable lens capsule without inadvertently aspirating, puncturing, or otherwise damaging the posterior capsule or other ocular cells. Therefore, the embodiments of the present disclosure avoid the post-operative complications associated with posterior capsulotomy. Moreover, the embodiments of the present disclosure allow for the disruption of lens epithelial cells without applying energy through an IOL, thereby avoiding the damage to the IOL that may arise during treatment of PCO during laser treatment. In addition, the embodiments of the present disclosure allow for prophylactic treatment of ACO and PCO during the initial cataract extraction surgery, thereby reducing the number and cost of surgical procedures the patient may have otherwise had to undergo. Also, the embodiments of the present disclosure eliminate the need for a separate handpiece and/or surgical system to prevent PCO after removal of a lens by a conventional ECCE. Thus, the embodiments of the present disclosure facilitate IOL exchange, ACO reduction, and PCO reduction.

As disclosed herein, in some embodiments, a capsule expander system, for inserting a capsule expander within a lens capsule of an eye of a patient, may include: (a) an annular capsule expander configured to stabilize within and to expand the lens capsule when in an expanded condition, the capsule expander comprising a circumferentially tapered profile wherein a center portion of the capsule expander includes a first height and an outermost peripheral portion of the capsule expander includes a second height that is less than the first height, the capsule expander comprising an outer, convex surface and an inner, concave surface, wherein the inner surface includes an IOL engagement feature shaped and configured to stabilize and center an IOL within the capsule expander; and (b) a delivery instrument configured to position the capsule expander in the eye. The delivery instrument may include: (a) a lumen with a longitudinal axis, the lumen sized to receive the capsule expander in an unexpanded condition; and (b) a plunger longitudinally disposed within the lumen, the plunger configured to translate longitudinally within the lumen to displace the capsule expander from the lumen. In some embodiments, the capsule expander includes a predetermined shape configuration selected from a group including a closed, arcuate shape and an open, arcuate shape. In some embodiments, the capsule expander in an expanded condition is configured to prevent an anterior capsule from contacting a posterior capsule of the lens capsule. In some embodiments, the capsule expander comprises a self-expanding biocompatible material. In some embodiments, the capsule expander comprises a material having shape memory. In some embodiments, the capsule expander comprises a plurality of orifices spaced circumferentially around the capsule expander. In some embodiments, the capsule expander comprises raised rim portions at the center portion that are angled away from the outermost peripheral portion and configured to contact the lens capsule. In some embodiments, the raised rim portions include a contact surface forming a right angle with the peripheral portion. In some embodiments, the capsule expander includes an external diameter sized to match an internal diameter of an equatorial region of the lens capsule in the eye. In some embodiments, the outer surface is configured to conform against an inner surface of an equatorial region of the eye. In some embodiments, the capsule expander is shaped and configured to self-expand upon emerging from the delivery instrument.

As further disclosed herein, in some embodiments, a method for stabilizing a lens capsule of an eye and inhibiting opacification of the lens capsule may include: (a) inserting a capsule expander in an unexpanded condition into a lumen of a delivery instrument sized to receive the capsule expander, wherein the capsule expander has a circumferentially tapered profile in an expanded condition, and wherein the delivery instrument comprises a plunger longitudinally disposed within a lumen; (b) moving the plunger along a longitudinal axis of the lumen toward a distal end of the delivery instrument to displace the capsule expander from the lumen of the delivery instrument into the lens capsule and allow the capsule expander to assume the expanded condition; and (c) positioning the capsule expander against an equatorial region of the lens capsule such that the capsule expander is centered within the lens capsule and the capsule expander separates an anterior capsule and a posterior capsule of the lens capsule. In some embodiments, the capsule expander comprises raised rim portions, and positioning the capsule expander against an equatorial region of the lens capsule comprises positioning the raised rim portions against an inner surface of the lens capsule. In some embodiments, the method may further include inhibiting migration of lens epithelial cells across the inner surface of the lens capsule beyond the raised rim portions. In some embodiments, the method may further include inserting an IOL within the capsule expander.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An implantable capsule expander device for insertion within a lens capsule of an eye of a patient, the device comprising:
   an arcuate center portion including first and second circular rims and having a first height, and wherein the first rim includes a circular raised contact surface configured to contact an inner surface of the lens capsule;
   an outermost peripheral portion including a second height that is less than the first height, wherein the center portion and the outermost peripheral portion are configured to stabilize the capsule expander device within the lens capsule and to expand the lens capsule, and wherein the outermost peripheral portion comprises a mesh-like configuration of orifices extending from an inner surface to an outer surface of the peripheral portion and spaced circumferentially around the peripheral portion; and
   a receiving portion sized to receive an artificial intraocular lens, the receiving portion formed between the first and second rims, wherein the implantable capsule expander device is symmetric with respect to a plane parallel to the first and second rims and positioned halfway therebetween.

2. The capsule expander device of claim 1, wherein the peripheral portion comprises a plurality of orifices spaced circumferentially around the peripheral portion, such that the plurality of orifices are positioned to contact the inner surface of the lens capsule.

3. The capsule expander device of claim 1, wherein the center portion includes a predetermined shape configuration of an open, arcuate shape.

4. The capsule expander device of claim 1, wherein at least one of the center portion, the peripheral portion, and the receiving portion comprise a self-expanding biocompatible material.

5. The capsule expander device of claim 1, wherein at least one of the center portion, the peripheral portion, and the receiving portion comprise a material having shape memory.

6. The capsule expander device of claim 1, wherein the peripheral portion comprises a plurality of orifices spaced circumferentially around the peripheral portion.

7. The capsule expander device of claim 6, wherein the plurality of orifices are symmetrically or non-symmetrically spaced around the peripheral portion.

8. The capsule expander device of claim 1, wherein the first and second rims are angled away from the peripheral portion and the second rim has a circular raised contact surface configured to contact the lens capsule.

9. The capsule expander device of claim 8, wherein the raised contact surfaces of the first and second rims form right angles with the peripheral portion.

10. The capsule expander device of claim 8, wherein the raised contact surfaces of the first and second rims are textured.

11. The capsule expander device of claim 1, wherein raised contact surface of the first rim has a curvature corresponding to a curvature of an inner surface of the lens capsule.

12. The capsule expander device of claim 1, wherein the peripheral portion includes an external diameter sized to match an internal diameter of an equatorial region of the lens capsule in the eye.

13. The capsule expander device of claim 1, further comprising an outer, convex surface and an inner, concave surface, wherein the receiving portion is positioned on the inner, concave surface.

14. The capsule expander device of claim 13, further comprising an IOL engagement feature on the receiving portion of the inner surface, wherein the IOL engagement feature is shaped and configured to stabilize and center an IOL within the capsule expander device.

15. The capsule expander device of claim 13, wherein the outer surface is configured to conform against an inner surface of an equatorial region of the eye.

16. The capsule expander device of claim 13, wherein the outer surface includes a first angle of curvature and the inner surface includes a second angle of curvature, and the first angle of curvature substantially matches the second angle of curvature.

17. The capsule expander device of claim 1, wherein the receiving portion is sized to receive more than one artificial intraocular lens.

18. The capsule expander device of claim 1, wherein the outer peripheral portion comprises a series of oblong orifices extending around the outer peripheral portion, wherein each of the oblong orifices is symmetric about the plane.

19. An implantable capsule expander device for insertion within a lens capsule of an eye of a patient, the device comprising:
   an arcuate center portion including first and second circular rims and having a first height, and wherein the first rim includes a circular raised contact surface configured to contact an inner surface of the lens capsule;
   an outermost peripheral portion including a second height that is less than the first height, wherein the center portion and the outermost peripheral portion are configured to stabilize the capsule expander device within the lens capsule and to expand the lens capsule and wherein the outermost peripheral portion and the center portion are configured in an open, arcuate shape; and
   a receiving portion sized to receive an artificial intraocular lens, the receiving portion formed between the first and second rims, wherein the implantable capsule expander device is symmetric with respect to a plane parallel to the first and second rims and positioned halfway therebetween.

* * * * *